(12) United States Patent
Kahl et al.

(10) Patent No.: US 7,582,264 B2
(45) Date of Patent: Sep. 1, 2009

(54) DEVICE FOR MICROFLUID ANALYSES

(75) Inventors: Johan-Valentin Kahl, Munich (DE);
Roman Zantl, Baldham (DE)

(73) Assignee: ibidi GmbH, Munich (DE)

( * ) Notice: Subject to any disclaimer, the term of this patent is extended or adjusted under 35 U.S.C. 154(b) by 138 days.

(21) Appl. No.: 10/589,307

(22) PCT Filed: Oct. 4, 2004

(86) PCT No.: PCT/EP2004/011052

§ 371 (c)(1),
(2), (4) Date: Feb. 9, 2007

(87) PCT Pub. No.: WO2005/079985

PCT Pub. Date: Sep. 1, 2005

(65) Prior Publication Data

US 2007/0272000 A1    Nov. 29, 2007

(30) Foreign Application Priority Data

Feb. 17, 2004  (DE) ................ 10 2004 007 646

(51) Int. Cl.
*B01L 11/00* (2006.01)
(52) U.S. Cl. ............................................. 422/101
(58) Field of Classification Search ............ 73/426, 73/432.1; 422/101–103; 435/297.1; 257/414
See application file for complete search history.

(56) References Cited

U.S. PATENT DOCUMENTS

| | | | |
|---|---|---|---|
| 4,756,884 A | | 7/1988 | Hillman et al. |
| 4,865,813 A | * | 9/1989 | Leon ........................... 422/101 |
| 5,116,759 A | * | 5/1992 | Klainer et al. ............ 435/287.2 |
| 5,327,033 A | * | 7/1994 | Guckel et al. ......... 310/40 MM |
| 5,665,599 A | | 9/1997 | Minuth |
| 5,961,932 A | * | 10/1999 | Ghosh et al. ................. 422/193 |
| 6,036,927 A | * | 3/2000 | Chatterjee et al. ............ 422/211 |
| 6,506,346 B1 | * | 1/2003 | Monro ........................ 422/102 |
| 6,806,543 B2 | * | 10/2004 | Yamakawa et al. .......... 257/414 |
| 7,005,109 B2 | * | 2/2006 | Husar .......................... 422/99 |
| 7,353,689 B2 | * | 4/2008 | Weckstrom ................ 73/19.12 |
| 2002/0061260 A1 | * | 5/2002 | Husar .......................... 422/100 |
| 2003/0194716 A1 | * | 10/2003 | Knoll ............................. 435/6 |
| 2003/0198130 A1 | | 10/2003 | Karp et al. |
| 2004/0053422 A1 | * | 3/2004 | Chan et al. ................... 436/180 |
| 2004/0219072 A1 | * | 11/2004 | Yamakawa et al. .......... 422/100 |
| 2004/0258571 A1 | * | 12/2004 | Lee et al. ..................... 422/100 |
| 2005/0019231 A1 | | 1/2005 | Kahl |
| 2005/0129580 A1 | * | 6/2005 | Swinehart et al. ........... 422/100 |
| 2005/0164373 A1 | * | 7/2005 | Oldham et al. ............ 435/287.2 |
| 2008/0019879 A1 | * | 1/2008 | Schleifer ..................... 422/102 |
| 2008/0047330 A1 | * | 2/2008 | Whitehouse et al. ....... 73/61.48 |

FOREIGN PATENT DOCUMENTS

| | | |
|---|---|---|
| DE | 4334677 C1 | 7/1994 |
| DE | 4443902 C1 | 4/1996 |
| DE | 10148210 A1 | 4/2003 |
| WO | 98/06496 A1 | 2/1998 |
| WO | 03/041862 A1 | 5/2003 |

\* cited by examiner

*Primary Examiner*—John Fitzgerald
(74) *Attorney, Agent, or Firm*—IP Strategies

(57) ABSTRACT

The invention relates to a device for microfluid analyses for a substrate with plane base surface and cover surface, wherein a chamber is integrated in the substrate for receiving liquid with at least two admissions and a semipermeable or permeable membrane is arranged in the chamber, wherein the chamber is subdivided by the membrane into two sectional chambers with at least one admission each.

33 Claims, 5 Drawing Sheets

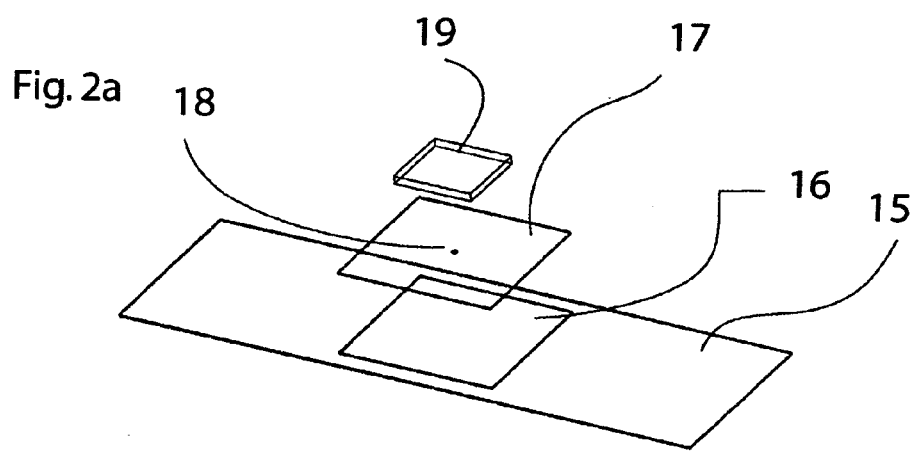
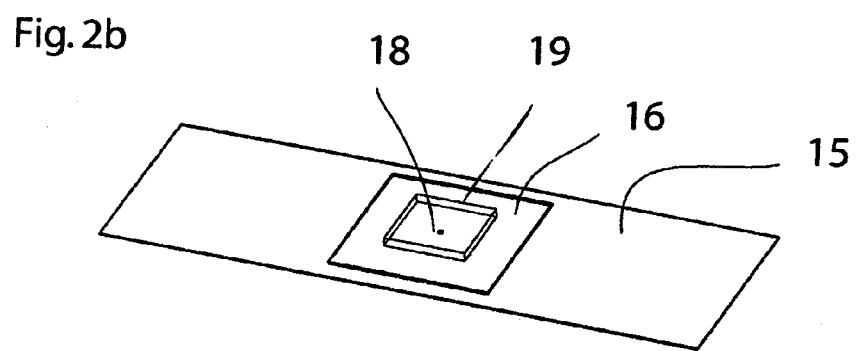

DEVICE FOR MICROFLUID ANALYSES

FIELD OF THE INVENTION

The invention relates to a device for microfluid analyses with a substrate with plane base surface and cover surface, in particular for microscoping cells as well as for molecular analysis.

BACKGROUND OF THE INVENTION

Microscopic analyses of cells (bacteria) or molecules are conventionally performed on microscope slides, cover glasses, Petri dishes, multititer plates or in cell culture bottles. Furthermore, carrier systems with liquid receivers, such as reservoirs or channels, are known from prior art. Such carrier systems are disclosed, for example, in DE 43 34 677 or in DE 201 16 019. These are bonded glass systems or plastic chambers in the form of a channel accessible to optical microscopy.

However, these carrier systems have the disadvantage that after a solution with the particles to be microscoped has been filled in, no more experiments can be performed, such as the selection of certain particles or migration studies, except for the addition of solutions. Such experiments have to be performed before the carrier system is filled which on the one hand prolongs the overall examination period and on the other hand involves the risk of a contamination due to decantation.

BRIEF SUMMARY OF THE INVENTION

Therefore, the object underlying the invention is to provide a device for microfluid analyses with which particle tests, such as the selection of certain particles or migration tests, and subsequent microscoping can be simply and precisely performed.

This object is achieved by the subject matter of claim 1. That means, according to the invention, a device for microfluid analyses with a substrate with plane base and cover surfaces is provided, wherein a chamber for receiving liquid comprising at least two admissions is integrated in the substrate, and a semipermeable or permeable membrane is arranged in the chamber, the chamber being subdivided by the membrane into two sectional chambers with at least one admission each.

A semipermeable membrane is a membrane which is permeable from only one side and/or particle selective permeable.

First, particles in solution can be filled into the device according to the invention, and then analyses can be performed with the aid of the membrane (for example filter, dialysis and/or migration analyses), and subsequently microscopic analyses can be directly performed.

In case of filter analyses, a permeable or porous membrane can be provided of which the pore or pores are smaller than the particles to be filtered (for example bacteria), so that these are not admitted through the membrane. For dialysis analyses, a semipermeable membrane can be preferably provided, which is, for example, not permeable for cells but for biomolecules, such as proteins or salts. A sectional chamber can then serve for the cultivation and microscopy of the cells or bacteria, respectively. Furthermore, the device according to the invention can be used for migration studies, in particular chemotaxis analyses, a distinction being made between horizontal chemotaxis (i. e. in parallel to the permeable membrane) and vertical chemotaxis (i. e. perpendicular to the membrane).

According to an advantageous further development, the sectional chambers can be at least partially arranged in parallel one to another. This can be achieved by a suitably embodied chamber and/or a suitably arranged membrane. Due to a parallel extension of the sectional chambers, a large interface between the sectional chambers is obtained by which the particle exchange can be accelerated.

Preferably, the sectional chambers can be arranged in a plane in parallel or perpendicularly to the base surface of the substrate.

According to an advantageous further development, the membrane can be arranged at least partially in a plane in parallel or perpendicularly to the base surface of the substrate. Thus, the resulting sectional chambers are then at least partially arranged in a plane perpendicularly or in parallel to the base surface of the substrate. This arrangement can be in particular selected depending on the desired application. An arrangement of sectional chambers one upon the other (membrane in parallel to the base surface) can be advantageous if, for example, a gravitation effect on the particles towards the membrane is desired. In an arrangement of the sectional chambers one next to the other (membrane perpendicularly to the base surface), in particular both sectional chambers are equally simply accessible with the microscope.

Advantageously, the membrane can be flexible, preferably elastic. With a flexible (pliant) membrane, the shape of the sectional chambers can be changed; an elastic membrane permits a reversible change of the volume of the sectional chambers by applying pressure to the membrane.

In an advantageous further development, the first of the two sectional chambers can comprise a grid. In this case, the grid as mechanical reference can serve for maintaining the particles to be detected in a focal plane.

Further, in case of a fluid flow from the second into the first sectional chamber, the membrane can be partially or completely pressed against the grid. In a fluid flow, particles are transported in a liquid or a gas. The grid additionally serves for keeping the membrane plane in the fluid flow or for preventing the membrane from being shifted or from tearing. Here, it is possible that a thin fluid film remains between the grid and the membrane, possibly even if air is pressed behind the fluid flow, so that the fluid film holds together the membrane and the grid. The mesh size of the grid or the diameter of the holes is preferably selected such that the membrane is not pressed deeper into the meshes or holes than the focal depth of the read-out apparatus during the filter operation.

The surface of the membrane functioning as filter can be continuously smooth, at least partially perforated and/or at least partially permeable.

Further, the membrane can be firmly provided between the first and second sectional chambers.

This can be permitted by the membrane being glued in under tension. However, in the process, there can be a problem that the filter membrane tears when strongly curing adhesives are used. This is in particular the case as soon as the membrane is contacted with solvents that make itself or the surrounding structures swell or shrink. This problem can be solved by using elastic polymers with low Shore hardnesses, e. g. below 60, such as silicone, for a firm, i. e. conglutinated, mounting. For doing so, one can place a line of silicone, preferably into a groove, onto which the edge of the membrane is then pressed. Alternatively, one can also use soft polymer structures in order to clamp the membrane such that it is at least partially tightened during the clamping process.

Moreover, this risk of a tearing of the membrane can be reduced by letting the membrane rest on the grid in this case, too, during the filter process when the fluid flows from the second sectional chamber into the first sectional chamber through the membrane towards the grid. In this case, the grid has a small defined distance to the membrane when no fluid pressure is applied.

Alternatively, it is possible to arrange the membrane loosely between the first and the second sectional chambers.

In this case, it can be advantageous to provide a means that positions the membrane such that it partially or completely lies in the fluid flow. In the process, the fluid flow can hit the membrane nearly perpendicularly before the same is pressed against the grid.

The means for positioning the membrane is to ensure that the fluid flowing out of the admission of the second sectional chamber into the first sectional chamber gets below the membrane (i.e. from the base surface of the second sectional chamber) and thereby presses the same against the grid.

This can be ensured, for example, by a groove situated between the admission of the second sectional chamber and the grid in which groove the edges of the membrane are held at least partially. Alternatively, this can also be realized by a notch, a bulging or the like.

In a further advantageous embodiment, the membrane can be arranged such that it is partially or completely pressed against the base surface of the substrate/the second sectional chamber by a force, e. g. in case of a fluid flow from the first into the second sectional chamber. Here, the base surface can consist of a foil, preferably a plastic foil.

This can be done, for example, if the membrane is pressed against the grid by a fluid flow from the second chamber with the particles to be detected and then the filtering membrane is pressed to the base surface of the second sectional chamber by a short backflow (liquid flow, short gas thrust, or the like) from the admission of the first sectional chamber through the grid into the direction of the second sectional chamber. First, the membrane bulges towards the base surface with the backflow pressure, possibly partially touches the same (in the membrane center) as it still sticks with its edges, for example in the groove. If more pressure is applied by the backflow, the edges then also detach from the groove and the membrane completely lies against the plane base surface (even with its edges). In general, here, too, a thin fluid film can remain between membrane and base surface.

Alternatively, instead of the flowing fluid, magnetic forces or a stamp can also press the membrane to the base surface.

This device has the advantage that the particles filtered by the membrane are almost stationarily enclosed between the base surface (preferably a plastic foil) and the membrane, that means they can no longer be removed by normal mechanical loads. Further, a read-out apparatus can use the base surface as reference, i.e. as spacer to the membrane. The preset focus would in this case only go by the thickness of the base surface.

Usually, in case of strongly luminous particles (e. g. fluorescence beads), objectives with numerical apertures of less than 0.5 or optical apparatuses with similar characteristics can be used. Thus, the depth of field is in the range of approx. 10-200 $\mu$m. In case of weakly luminous particles, objectives with numerical apertures of up to 1.4 are typically used. Thus, layer thicknesses of a depth of up to 0.5 to 10 $\mu$m can be represented. Thus, in addition the necessary smoothness of the membrane is defined as all objects to be detected should be within this focal range.

In an advantageous further development, the membrane can be connected with the bottom of the chamber at least partially. For example, the membrane can be bonded or connected by means of ultrasonic bonding.

Further, positioning means can be provided in the substrate which are to fix the membrane when it is mounted.

Preferably, at least a part of the membrane can be detachably arranged so as to planely lie against a chamber wall, in particular the bottom of the chamber. If the membrane lies against a chamber wall it is simply and directly accessible to a microscope through this wall. For example, the membrane can first lie against a wall in the course of the examination, then liquid with the particles to be analyzed is placed between the wall and the membrane causing the membrane to detach from the wall. A part of the liquid and/or the particles passes the membrane, while another part gets stuck to the membrane, for example in the pores. As soon as the pressure on the membrane by the liquid is reduced, the same again lies against the wall of the chamber due to its arrangement and/or elasticity, so that its surface with the particles arranged thereon can be microscopically analyzed.

According to a further development of the devices described above, the membrane can have at least one pore, wherein each pore can have a pore diameter in a predetermined partial area of the area of 1 nm to 20 $\mu$m, preferably 0.5 $\mu$m to 20 $\mu$m. The partial area can in particular also comprise the complete mentioned area or only a certain value from the area.

Depending on the diameter or the diameter distribution of the pores, the particle selectivity of the membrane and/or the flow through the membrane can be controlled.

In a particular embodiment, the pores can be arranged at a regular distance from one another. The pore distance can be between 5 $\mu$m and 2 cm. In a preferred embodiment, the pore pattern can represent all known two-dimensional crystal textures. The number of pores in an analysis reservoir can be up to 50,000. The analysis reservoirs can typically have a size between 5 $\mu m^2$ and 5 $cm^2$. In a preferred embodiment, between one and 8192 reservoirs are accommodated on one carrier.

The pores can form a regular pattern. In a typical experiment, chemotactically activatable cells are placed on the membrane with the regularly arranged pores and there uniformly distribute on the membrane surface as long as no chemotaxins diffuse through the pores and get into contact with the cells.

If chemotaxins diffuse through the pore, the cells start to move towards the closest pores. After a certain time, all cells have gathered at the respective pores.

The difference between the equipartition of the cells before the action of the chemotaxins and the agglomeration of the cells around the pores after the addition of the chemotaxins can be quantified by means of Fourier analysis. The equipartition of the cells appears as a straight line in the Fourier space. The periodic arrangement of the cells around the pore appears as "delta-like" function at the value in the Fourier space corresponding to the pore distance. This method is in particular reasonable if the identical chemotaxin with the identical concentration diffuses through all pores. In particular, a quantitative and time resolved statement can be made on the cell movement if the transition from the straight line to the delta function is analyzed as a function of time. This method also offers a simple and fast averaging on the behavior of many cells (improvement of statistics). In a further development, the optically visible pores can be used as a scale in the Fourier space.

In another further development, various chemotaxins can diffuse through the pores, so that a direct comparison of the efficacy can be represented. Equally, identical chemotaxins can be used in varying concentrations in order to detect a more accurate analysis of the migration speed.

In another further development, various pore arrays can be accommodated in various reservoirs.

If the reservoirs are designed as channel, the liquid can be locked in this channel. Due to the surface tension of the liquid, the liquid then does not move out of the channel, even if the channel is turned. For this, the liquid completely fills the channel up to the respective outlets. Typically, the channel has a height of between 10 μm and 1 cm and a width of between 10 μm and 5 cm. The length can be between 100 μm and 30 cm.

In a further development, the pore patterns can represent all known two-dimensional crystal textures. The number of pores in an analysis reservoir is between at least two and can be up to 50,000. The analysis reservoirs can typically have a size of between 5 μm$^2$ and 5 cm$^2$. In a preferred embodiment, between one and 8192 reservoirs are accommodated on one carrier.

The pores can also form irregular patterns. For analyzing the cell distribution as a function of time and thus the cell movement, the correlation function between the image of the holes and the image of the "chemotaxed" cells can be used. The holes can be generated e. g. by neutron bombardment and subsequent etching.

The membrane of the above mentioned devices can preferably comprise an optically high-grade material. With an optically high-grade material (i. e. without double refraction or autofluorescence or with an autofluorescence or double refraction equal to or lower than that of COC or COP), optical analyses, in particular on both sides of the membrane, can be performed in an improved manner.

According to an advantageous further development, the chamber can comprise at least four admissions and be subdivided into two sectional chambers with at least two admissions each by the membrane. Thus, each sectional chamber can be fluidically addressed independently of the other one, i. e. each of the chambers has an own inlet and outlet.

Further, at least one of the admissions can annularly surround the chamber in order to ensure a uniform filling of the chamber.

Advantageously, the membrane and/or one chamber wall can comprise a surface functionalization. Thereby, in individual areas, certain processes, such as cell growth or adhesion of particles, can be favored. Different areas of the membrane or the chamber wall can have different surface functionalizations.

Preferably, the surface functionalization can comprise a coating, in particular with at least one polyelectrolyte film, one adhesion factor, one functional group, one lipid membrane, one cell layer and/or one blocking molecule.

The polyelectrolyte films can comprise PAA (polyacrylic acid), PEI (polyethylene diimide) and/or PSS (polystyrene sulfonic acid); the biomolecules can comprise proteins or DNA and the adhesion factors can comprise RGD peptides. The functional group can comprise COOH or NH$_2$, and the blocking molecule can comprise BSA, gelatin or DNA.

Preferably, the substrate of the above described devices can comprise plastics, in particular optically high-grade and/or optically non-transparent plastics. Optically high-grade (i. e. without double refraction or autofluorescence) plastics reduces interfering influences of the substrate, for example in fluorescence analyses; by the use of an optically non-transparent material, interferences due to undesired incident light from outside can be avoided.

Preferably, the substrate can comprise a covering element in the base surface of which a recess for the chamber is provided. In particular, the recess can be designed in the form of a dig. This permits a simple manufacture of the substrate.

The covering element can be a cover plate. In this case, the covering element is one piece and can be easily manufactured.

Alternatively, the covering element can be an intermediate plate in which an opening for the chamber is provided, and a cover plate which is provided for covering the opening on one side of the intermediate plate. In this case, the covering element comprises two plates, that is an intermediate plate and a cover plate. The cover plate can comprise a receiver on the side facing the intermediate plate. Thus, then the shape of the chamber is determined by the recess in the cover plate and the shape of the opening. Alternatively, the cover plate can have no recess, so that the complete recess of the covering element is determined by the opening.

The intermediate plate can be a plastic foil, in particular having a thickness of 1 μm to 1 mm.

Preferably, the membrane can be arranged between the cover plate and the intermediate plate. In this manner, the membrane can be particularly easily connected to the substrate, for example, by clamping it between the cover plate and the intermediate plate and/or by connecting it with at least one of these two (partial) plates by gluing, ultrasonic bonding or the like. If the cover plate itself also has a receiver, thus a sectional chamber is formed by the receiver in the cover plate and separated from the other sectional chamber which is formed by the opening in the intermediate plate by means of the membrane (partition).

According to an advantageous further development, the substrate can comprise a cover element for covering the recess. The same forms the remaining wall of the chamber which is formed by the recess, with or without intermediate plate.

Advantageously, the cover element can be a plastic foil, in particular of optically high-grade plastics and/or with a thickness of 50 μm to 1 mm. On the one hand, a plastic foil can be easily connected to the covering element, and on the other hand, by the use of a foil, very low thicknesses of the cover element can be achieved, thus improving the quality of microscopic analyses.

Preferably, the admissions can end in the cover surface of the covering element of the substrate. Thus, the chamber or the sectional chambers are each accessible from above for addition of liquid.

According to an advantageous further development, furthermore at least one liquid reservoir can be provided which is arranged on the covering element of the substrate and into which an admission ends. Such a liquid reservoir can serve for discharging relatively large amounts of liquid into the chamber or it can serve as overflow if it is arranged at the port of the outlet.

Preferably, the at least one liquid reservoir can be made of plastics, preferably the same plastics as the covering element in the area of the admission port. According to a preferred further development, the liquid reservoir and the covering element can be formed in one piece in the area of the admission port. This means that the reservoir is not for example glued or screwed with the covering element. In this manner, seals between the reservoir and the covering element can be avoided and the risk of a contamination is reduced.

Preferably, the one piece can be a molded part. This permits a simple manufacture of the substrate.

Preferably, the substrate can be designed in a microscope slide or multititer format.

All above described devices can be further developed to the effect that the base and/or cover surface and/or membrane consist of an optically high-grade material which has such a low or a lower autofluorescence as/than COC (cyclic olefin copolymers) or COP (cyclic olefin polymers).

Preferably, the cover surface and/or base surface each can also consist of a plastic foil.

In this case, the base or cover surface can also consist of an optically high-grade material. "Optically high-grade" means that the base surface is optically transparent or has an autofluorescence equal to or lower than that of COC or COP or has no double refraction or is transparent in UV light.

In order to determine the autofluorescence, measurements have been performed with the Axivert S 100 of Zeiss, the HBO 50 lamp and the 40 X Plan Neofluar Objective of Zeiss (NA 0.75) as well as the Filtersatz 09 of Zeiss (excitation 450-490 nm, emission 515-565 nm) in a dimmed room at room temperature. All relevant adjustments, in particular the adjustments of the HBO lamp, as well as the position of the lamp field stop were not changed during measurement.

The measuring range was 219×173 µm. With the software IPLab (Scanalytics), the exposure was performed at a 2×2 Binning 500 ms and an offset of 200 was adjusted at the 5 MHz MicroMax Camera of Princeton Instruments (Austin/Tex.).

Materials with a thickness between 150 µm and 200 µm were used and focused in the center of the preparation.

With this adjustment, a medium pixel value of 64±3 was determined with glass (Menzel glasses 25×75 mm) with a thickness of 170 µm±5 µm.

The foil thickness with the used COC was 190 µm±5 µm, and a medium pixel value of 97±5 was determined. With the used COP, the foil thickness also was 190 pm±5 µm, and a medium pixel value of 107±6 was determined. Under these conditions, in particular with the used filters, all values with an autofluorescence of less than 120 are to be assessed as "low autofluorescence".

With the use of filter sets with an excitation wave length as of 529 nm, with this construction no significant differences between glass, COC and COP were determined.

BRIEF DESCRIPTION OF THE DRAWINGS

Further features and advantages of the invention are described below with reference to the examples and figures:

FIG. 2a, 2b illustrates an example of a device for chemotaxis;

FIG. 3b shows a cross-sectional view of the device of FIG. 3a;

DETAILED DESCRIPTION OF THE INVENTION

Figure 1:
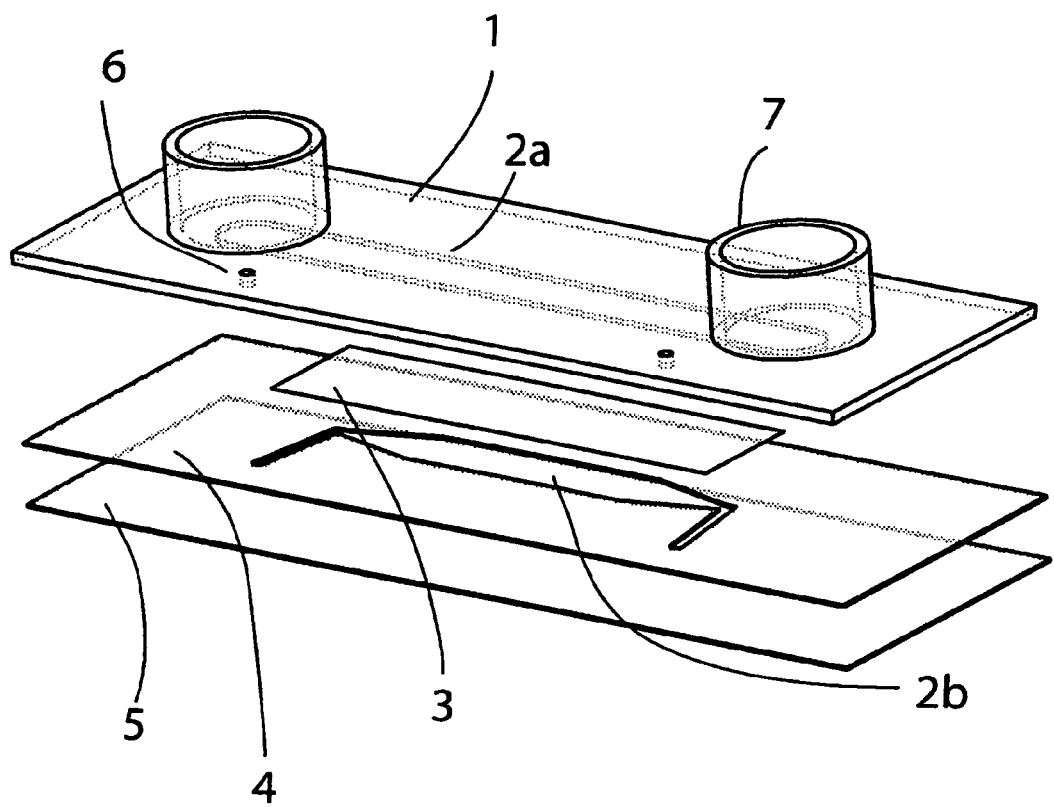
FIG. 1 shows an exploded view of a device for microfluid analyses with a substrate with a cover plate and an intermediate plate.

In FIG. 1, a device for microfluid analyses is shown in an exploded view. The device comprises a substrate which in turn comprises a covering element with a cover plate 1 and an intermediate plate 4. In the base surface of the cover plate, a recess 2a is provided of which the admissions (not shown) each end in a liquid reservoir 7. The intermediate plate 4 comprises an opening 2b. This opening is designed such that on the one hand it is located under the recess 2a of the cover plate and on the other hand comprises admissions which end in the cover surface of the cover element 1 at the openings 6.

Furthermore, the substrate comprises a cover element 5 which can be in particular designed as foil. The intermediate plate 4, too, can be designed as plastic foil. In FIG. 1, a membrane 3 is arranged between the cover plate 1 and the intermediate plate 4, so that after joining and connecting the cover plate 1, the intermediate plate 4 and the cover element 5, two sectional chambers are formed which are separated by the membrane 3. In the process, the two sectional chambers are each formed by the recess 2a and the opening 2b, respectively, and the membrane 3 arranged in-between, so that below the sectional chambers are also designated with 2a and 2b, respectively.

In this case, the membrane can be easily clamped between the cover plate 1 and the intermediate plate 4 or connected with one of these or both plates, for example by gluing or ultrasonic bonding.

For example, Cyclopor Track Etched Membranes from Whatman or filter membranes from Millipore can be used.

That means, the resulting device for microfluid analyses comprises a chamber, formed by the recesses 2a and the opening 2b, which chamber is subdivided into two sectional chambers in the form of channels by the membrane 3. Each of the two sectional chambers has its own inlet and outlet lines.

The device according to the invention and in particular the device shown in FIG. 1 can be in particular used for dialysis experiments. In the case of the device shown in FIG. 1, the sectional chamber 2a would be the dialysis channel and the sectional chamber 2b the observation channel which are separated by a semipermeable membrane 3. The lower observation channel 2b can, for example, be filled with suspension culture via one of the openings 6 and the upper channel 2a can be filled via the reservoirs 7. The membrane is then selected such that it is impermeable for cells, however permeable for biomolecules, such as proteins and salts.

By the shown arrangement, the exchange through the semipermeable membrane can be dominated by diffusion or convection. The larger the contact surface between the two sectional chambers is, the quicker the exchange takes place.

Alternatively to the shown embodiment in which the two sectional chambers extend in parallel one to another and lie in a plane perpendicular to the base surface, the sectional chambers can also be arranged one next to the other in a plane in parallel to the base surface.

In one possible application, adherent cells are brought into contact with a surface (wall) to which cells adhere by specific interaction at certain bonding sites. A solution is flushed through the dialysis membrane 3, the solution having a predetermined concentration of antibodies. The antibodies are selected such that they specifically bind to the binding sites of the cells. The antibodies compete with the extracellular binding molecules of the cells for the binding sites immobilized on a wall, leading to a detachment of the cells if the antibody concentration is sufficient. In contrast to conventional cell culture vessels or microscopy carriers, the antibodies can now be diluted via the dialysis membrane until the cells again have the possibility of adhering to the surface. By this, one can, for example, study the reversibility of bonds between cells by means of cell substrate interactions.

In a further application, cells in suspension cultures can be analyzed. Cells in suspension culture are in general obtained by centrifugation, subsequent removal of the supernatant and resuspension of ingredients of the buffer or the nutrient solution in a purified form. For an effective purification, it is often necessary to repeat these operations several times.

By the use of the shown device, it is possible to contact cells in suspension culture with certain substances or to liberate the cell medium from these. For example, cells in suspension culture can be provided with substances in the observation channel 2b which are produced by a cell culture growing in the dialysis channel 2a, the two cell cultures not being mixed. This technique can, for example, be used if poorly growing cells require the substances of so-called feed cells in order to be better cultivated in vitro. The feed cells can be removed and added again at any time by the independent fluid access of both sectional chambers in order to reduce, for example, cross reactions with the actual experiment.

In a further application, the device shown in FIG. 1 can be used to form a model system for sepsis. In the process, a human cell culture is cultivated in the observation channel and a bacteria culture is cultivated in the dialysis channel 2a. The human cells are poisoned by the bacteria. With the shown device, one can analyze which medicine can keep the human cells alive with a certain bacteria density.

In addition to the mentioned applications, the membrane can be used in such a device for migration studies, in particular for chemotaxis analyses. In chemotaxis, cells move in a chemical concentration gradient. Here, one can distinguish between horizontal chemotaxis (in parallel to the membrane) and vertical chemotaxis (perpendicular to the membrane).

In horizontal chemotaxis, cells are incorporated into a sectional chamber and adhere on the surface of the membrane. A solution with a certain chemical (for example C-AMP) is filled into the other sectional chamber. The solution diffuses from the second into the first sectional chamber through the pores of the membrane and there forms a radial concentration gradient around the pore. Then, the reaction of the cells situated there on the concentration gradient can be analyzed. For this experiment, the membrane preferably has one or more pores with predetermined pore diameter and predetermined hole distance.

For such chemotaxis analyses, a membrane can have only one pore or a hole having a size of 1 nm to 30 μm. In this case, on one side of the membrane (e. g. underneath the membrane) cells can be provided in a holding medium. For example, cells can be incorporated in agar or agarose. Instead of agar or agarose, other holding media can also be used. The holding media serve among others for improving the optical analysis of the cell dynamics.

On the other side of the membrane (for example above the membrane) molecules (chemotaxins) which are also embedded in a holding medium can be provided. Due to this, for the analysis, no micropipette with pressure control has to be used as the concentration of the chemotaxins remains constant depending on the volume of the holding medium if the chemotaxins diffuse through the hole. By diffusion of these chemotaxins from the first side of the membrane through the hole to the second side of the membrane, a spatially and chronologically defined concentration gradient is formed on the second side of the membrane. Thus one can analyze how and if the cells embedded on the second side react to the concentration gradient. The membrane is preferably air permeable.

In FIGS. 2a and 2b, a possible example of a corresponding device is represented. Basically, for this examination the use of a flow chamber is not necessary. In FIG. 2a, a corresponding construction is shown in an exploded view. On a base plate 15, an area wetted with a holding medium for cells (e. g. agarose) is applied. In this area, the cells to be analyzed are located. A membrane 17 with only one hole 18 separates this area from the holding medium 19 enriched with the chemotaxins. FIG. 2b shows the assembled analysis carrier.

Such holding media, however, can also be provided in a device according to the invention. For this purpose, the holding media can be each provided in the sectional chambers which are separated by the membrane. For example, the membrane can represent the upper and bottom side of two channels arranged in a substrate, analogously to the example shown in FIG. 1. Alternatively, several, typically 2-96, reservoirs separated by membranes with a hole can be provided as little pots on a carrier or by a channel in a carrier.

With the vertical chemotaxis, the migration of cells in a chemical concentration gradient through a membrane is analyzed. In a typical application, for example a homogenous cell layer (cell type A) can be cultivated on a porous membrane. By the generation of a concentration gradient (filling the other sectional chamber with a solvent), the migration of another cell type (cell type B) through the cell layer can be analyzed.

The concentration of cell type B in the second sectional chamber can be detected, for example, by fluorescence techniques. Furthermore, the solution in the second channel can be withdrawn after a certain time and the concentration of cell type B can be determined. Analyses of leukocyte migrations through various cell layers in response to the concentration of various substances and the cell layer can thus be performed. In this case, the pore diameter is preferably 0.5 to 20 μm.

Figure 3A:
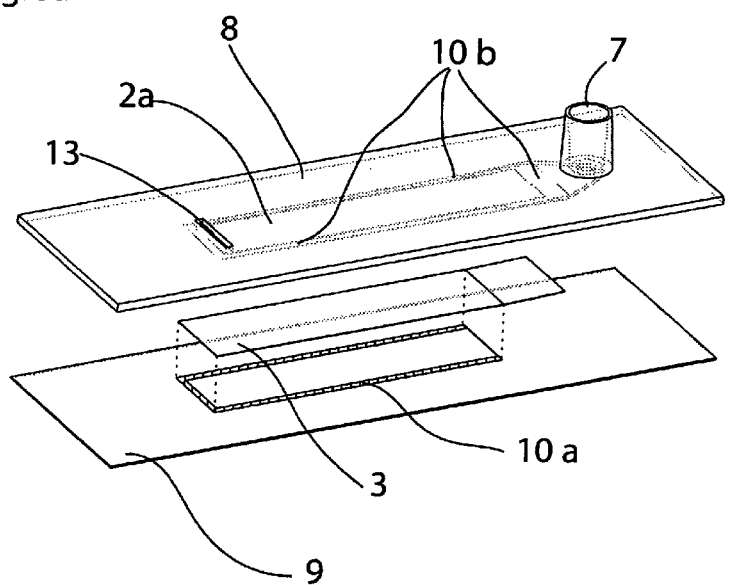
FIG. 3a shows an exploded view of a device for microfluid analyses with a cover plate and a membrane detachably arranged so as to planely lie against the bottom of the chamber.

In FIG. 3, another example of a device for microfluid analyses is shown in an exploded view. Here, the substrate comprises a cover plate 8 and a bottom foil 9 serving as cover element. In the cover plate 8, a recess 2a is provided which forms the chamber.

In the shown example, the chamber has only two admissions, one of them ending in a liquid reservoir 7 disposed on the cover plate and the other ending in the outlet opening 13.

Furthermore, a membrane 3 is provided which is glued with the foil 9 in the area 10a and with the cover plate 8 in the area 10b. As can be seen in the Figure, the membrane 3 is glued along its complete edge with the cover plate 8, while the membrane is not glued to the foil 9 at the side facing the reservoir 7. This means that liquid entering through the reservoir 7 has to pass the membrane 3 before it reaches the outlet opening 13.

As long as no liquid is filled into the chamber via the reservoir 7, the membrane planely lies against the foil between the glued areas.

Figure 3B:
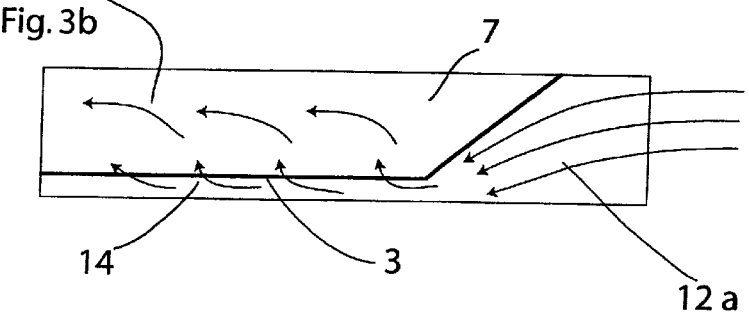
Figure 3C:
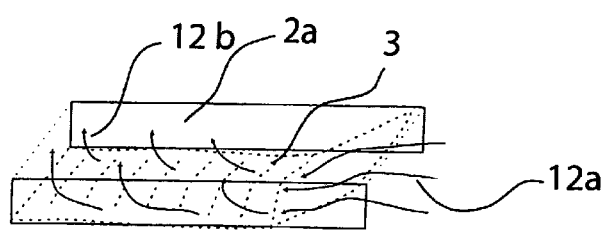
FIG. 3c illustrates a method with the device according to FIGS. 3a and 3b.
Figure 4A:
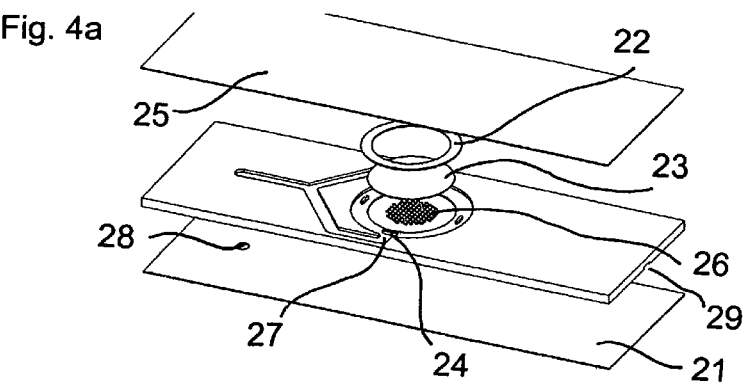
FIG. 4a-d shows an exploded view of a device for microfluid analyses with a grid and the assembly of the membrane.
Figure 4B:
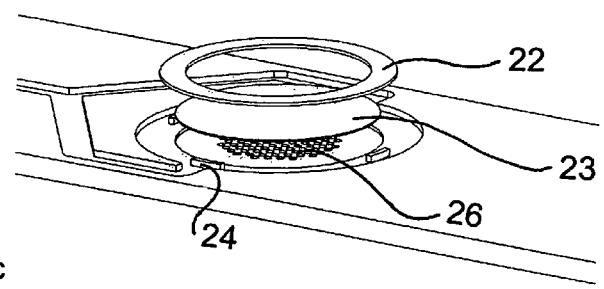
Figure 4C:
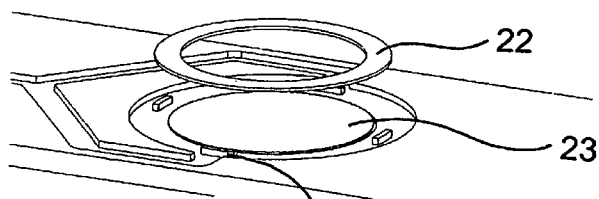
Figure 4D:
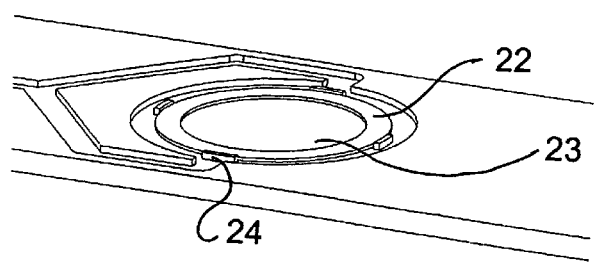

The membrane 3 subdivides the chamber into two sectional chambers, the first sectional chamber being located on the side of the admission and the second sectional chamber being located on the side of the outlet. The membrane is connected to the cover plate 8 such that the whole liquid filled in via the liquid reservoir 7 has to flow through the membrane in order to get to the outlet 13 through the sectional chamber 2a. By the filling in via the reservoir 7, the membrane is hit by pressure from the bottom, detaches from the bottom foil 9 and is pressed upwards. Preferably, the membrane is therefore elastic. This is shown in FIG. 3b in a side view and in FIG. 3c in a three-dimensional view.

In the shown Figures, the solution to be analyzed is designated with 12a before the filtering through the membrane and with 12b after the filtering.

If, for example, bacteria are in the solution which cannot pass the membrane 3, they agglomerate in the area 14 of the membrane. The filtered solution can escape through the outlet 13. After flushing with liquid, the membrane 3 again rests on the bottom foil 9 and can be microscopically analyzed from below. The bacteria can be, for example, colored with FISH (fluorescence in situ hybridisation).

In FIG. 4a-4d, a device for microfluid analyses is shown in an exploded view, and it is shown how the membrane is assembled in the device. The device comprises a cover plate 21 and a base surface 25, both in the form of a plastic foil, as well as a ring 22 for generating a groove in which the side edges of the membrane 23 have been built in by means of positioning means 24. The grid 26 is located between the membrane and the cover plate. Further, an annular admission 27 which serves the uniform filling of the chamber as well as an inlet 28 of the second sectional chamber and an outlet 29 of the first sectional chamber are represented.

In FIGS. 5a to 5d, a side view of the device of FIG. 4 is represented.

Figure 5:
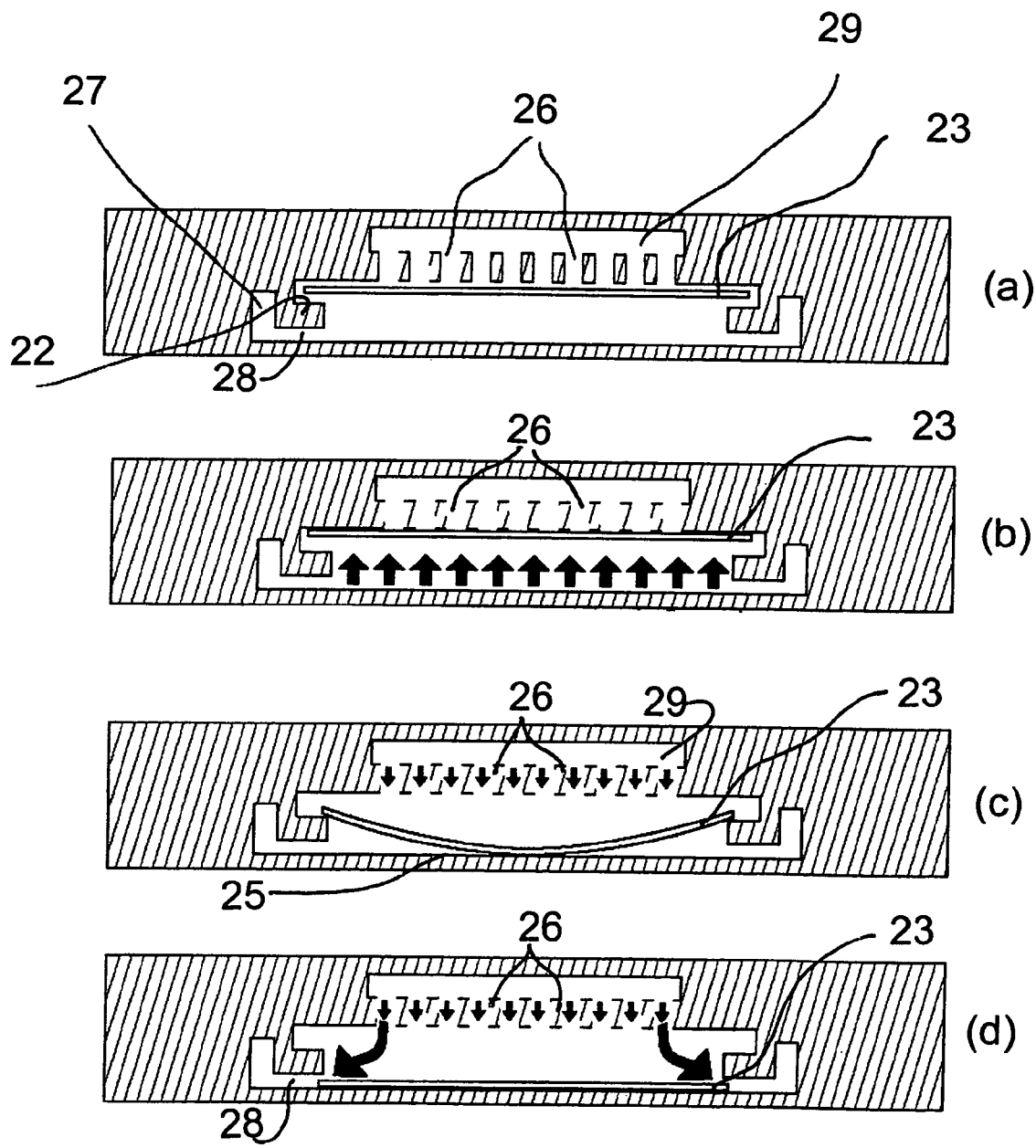
FIG. 5a shows a side view of the device in FIG. 4.
FIG. 5b illustrates in a side view of the device in FIG. 4 the fluid flow from the second sectional chamber towards the first sectional chamber.
FIG. 5c shows in a side view of the device in FIG. 4 the backflow of a fluid from the first sectional chamber towards the second sectional chamber.
FIG. 5d shows in a side view of the device in FIG. 4 the membrane after the backflow planely lying against the base surface of the second sectional chamber.

FIG. 5a shows the side edges of the membrane 23 in the groove generated by the ring 22 lying below the grid. The outlet 29 of the first sectional chamber is located at the top, the inlet 28 of the second sectional chamber is located at the bottom in the form of the annular channel 27.

In FIG. 5b, fluid flows from the inlet 28 in the direction of the arrow against the bottom surface of the membrane 23 and presses the same against the grid 26. At this moment, the particles to be analyzed are situated at the bottom surface of the membrane while the rest of the fluid flows through the membrane and the grid towards the outlet 29.

FIG. 5c represents the backflow, as a fluid hits the membrane 23 from the outlet 29 through the grid 26. The membrane bulges downwards towards the base surface 25 due to the pressure, but it is still fixed with its edges in the groove.

In FIG. 5d, the membrane 23 of FIG. 5c already completely lies against the base surface 25 due to the short backflow, so that now the backflow fluid can flow through the inlet 28 passing the membrane edges.

If, as described in FIG. 5d, the membrane 23 completely planely lies against the base surface 25, the membrane bottom surface with the filtered particles can be microscoped with high-resolution, preferably with a depth of field range of 0.5-200 μm.

If the liquid to be analyzed is blood, slurry or other samples where the bacteria have to separated from other solid ingredients, the surface of the membrane can be modified or functionalized, respectively, such that the bacteria adhere thereto. Preferably, however, an additional outlet opening that can be closed is provided for the bottom sectional chamber. The lower channel can then be flushed through this outlet opening in order to remove the other mentioned solid ingredients.

Preferably, the membrane of the device according to the invention has a large surface to permit fast flushing. In this case, however, the area of the membrane to be microscoped (analysis surface) is also relatively large. For this reason, the device according to the invention, in particular the examples in the Figures, can comprise a further chamber. In this case, then the particles to be analyzed as described above are filtered at the first membrane and subsequently collected in a further filter (analysis filter) by a backwash operation where a flow in the opposite direction is applied. This preferably has a smaller surface and can thus be microscopically observed more easily.

The further chamber is preferably connected with the corresponding sectional chamber by a closable opening (for example with a valve), so that only after the closable opening is opened (for example by applying a predetermined pressure on the valve by the backwash operation) the liquid which then only contains the particles which actually have to be analyzed is flushed into the further chamber. These bacteria are then filtered at the additional analysis membrane and can be microscopically analyzed there. Alternatively, the analysis membrane can be integrated in a lid which can close the inlet opening.

In embodiments comprising two admissions for one sectional chamber, such as shown in FIG. 1, the liquid admission into one sectional chamber can be effected by the two admissions simultaneously. In this case, the filtered particles mainly gather at the area of the membrane situated in the center between the two admissions. At this point, one can then analyze the particles.

For the various applications, the surfaces of the membrane and/or the chamber can be functionalized. For example, an improved cell growth on the membrane or on one of the internal chamber sides or walls, respectively, can be obtained by correspondingly treating the surface. In particular, a coating with polyelectrolyte films can be made which have typical thicknesses in the range of 5 nm to 100 nm. The coatings can consist of different polyelectrolyte films, such as PAA, PEI and PSS. In particular, a base layer each can consist of one of these materials. Biomolecules, such as proteins or DNA, can be directly applied onto these layers. Such a non-covalent bond is also stable when a flow is applied in the channel.

Unspecific or specific adhesion factors for molecules or cells (e.g. RGD peptides) can also be applied in the layer structure, in particular in the last layer applied. The last layer applied can contain functional groups, such as COOH or $NH_2$. These can be used for covalently coupling biomolecules.

After the binding of biomolecules onto the uppermost polyelectrolyte layer, a further layer for blocking unspecific bonds can be applied. This can be a further polyelectrolyte layer, a lipid membrane or a blocking molecule, such as BSA, gelatin or DNA. The applied biomolecule should maintain its binding capacity.

Furthermore, structured polyelectrolyte layers can also be provided. This can be done, for example, by spotting polyelectrolyte layers which makes it then possible to bind biomolecules or cells at special areas of the chamber or the membrane.

In addition, various areas or the different sectional chambers can be used with different polyelectrolyte layers.

Coating can then be effected, for example, by solving a polyelectrolyte in aqueous solution (approx. 0.1 mg/ml to 10 mg/ml) at a neutral pH. This solution is then flushed into the chamber and there incubated over a predetermined period (for example 10 minutes to 2 hours) at room temperature. In this manner, between one and twenty layers can be applied.

The invention claimed is:

1. Device for microfluid analyses with a substrate with plane base and cover surfaces, wherein
   a chamber for receiving liquid comprising at least two admissions is integrated in the substrate, and
   in the chamber a semipermeable or permeable membrane is arranged, the chamber being subdivided into two sectional chambers with at least one admission each by the membrane, wherein the substrate comprises a covering element, in the base surface of which a recess for the chamber is provided, and
wherein the covering element comprises an intermediate plate in which an opening for the chamber is provided, and a cover plate which is provided for covering the opening on one side of the intermediate plate.

2. Device according to claim 1, wherein the sectional chambers are at least partially arranged in parallel one to another.

3. Device according to claim 1, wherein the sectional chambers are arranged in a plane in parallel or perpendicularly to the base surface of the substrate.

4. Device according to claim 1, wherein the membrane is arranged at least partially in a plane in parallel or perpendicularly to the base surface of the substrate.

5. Device for microfluid analyses with a substrate with plane base and cover surfaces, wherein
a chamber for receiving liquid comprising at least two admissions is integrated in the substrate, and
in the chamber a semipermeable or permeable membrane is arranged, the chamber being subdivided into two sectional chambers with at least one admission each by the membrane,
wherein the substrate comprises a covering element, in the base surface of which a recess for the chamber is provided,
wherein the covering element is a cover plate, and
wherein the membrane is arranged between the cover plate and the intermediate plate.

6. Device according to claim 5, wherein the sectional chambers are at least partially arranged in parallel one to another.

7. Device according to claim 5, wherein the sectional chambers are arranged in a plane in parallel or perpendicularly to the base surface of the substrate.

8. Device according to claim 5, wherein the membrane is arranged at least partially in a plane in parallel or perpendicularly to the base surface of the substrate.

9. Device for microfluid analyses with a substrate with plane base and cover surfaces, wherein
a chamber for receiving liquid comprising at least two admissions is integrated in the substrate, and
in the chamber a semipermeable or permeable membrane is arranged, the chamber being subdivided into two sectional chambers with at least one admission each by the membrane,
wherein the substrate comprises a covering element, in the base surface of which a recess for the chamber is provided, and
wherein the substrate comprises a cover element for covering the recess.

10. Device according to claim 9, wherein the sectional chambers are at least partially arranged in parallel one to another.

11. Device according to claim 9, wherein the sectional chambers are arranged in a plane in parallel or perpendicularly to the base surface of the substrate.

12. Device according to claim 9, wherein the cover element is a plastic foil.

13. Device according to claim 12, wherein the plastic foil comprises optically high-grade plastics.

14. Device according to claim 12, wherein the plastic foil has a thickness of 50 µm 1 mm.

15. Device for microfluid analyses with a substrate with plane base and cover surfaces, wherein
a chamber for receiving liquid comprising at least two admissions is integrated in the substrate, and
in the chamber a semipermeable or permeable membrane is arranged, the chamber being subdivided into two sectional chambers with at least one admission each by the membrane,
wherein the substrate comprises a covering element, in the base surface of which a recess for the chamber is provided,
wherein the admissions end in the cover surface of the covering element of the substrate, and
wherein furthermore at least one liquid reservoir is provided which is arranged on the covering element of the substrate and in which an admission ends.

16. Device according to claim 15, wherein the base and/or cover surface and/or membrane consists of an optically high-grade material which has autofluorescence as low as or lower than COC or COP.

17. Device according to claim 15, wherein the sectional chambers are at least partially arranged in parallel one to another.

18. Device according to claim 15, wherein the sectional chambers are arranged in a plane in parallel or perpendicularly to the base surface of the substrate.

19. Device according to claim 15, wherein the membrane is arranged at least partially in a plane in parallel or perpendicularly to the base surface of the substrate.

20. Device according to claim 15, wherein the chamber comprises at least four admissions, and the membrane subdivides the chamber into two sectional chambers with at least two admissions each.

21. Device according to claim 15, wherein the membrane is flexible.

22. Device according to claim 21, wherein the membrane is elastic.

23. Device according to claim 15, wherein the membrane comprises at least one pore, each pore having a pore diameter in a predetermined partial area of the area of 1 nm-20 µm.

24. Device according to claim 23, wherein each pore has a pore diameter of 0.5 µm-20 µm.

25. Device according to claim 15, wherein the substrate comprise plastics.

26. Device according to claim 25, wherein the plastics includes at least one of optically high-grade plastics and optically non-transparent plastics.

27. Device according to claim 15, wherein the membrane and/or one chamber wall has a surface functionalization.

28. Device according to claim 27, wherein the surface functionalization comprises a coating.

29. Device according to claim 28, wherein the coating includes at least one of a polyelectrolyte film, an adhesion factor, a functional group, a biomolecule, a lipid membrane, a cell layer and a blocking molecule.

30. Device according to claim 15, wherein the at least one liquid reservoir is of plastics.

31. Device according to claim 30, wherein the at least one liquid reservoir is of the same plastics as the covering element in the area of the admission port.

32. Device according to claim 15, wherein the liquid reservoir and the covering element are formed in one piece in the area of the admission port.

33. Device according to claim 32, wherein the one piece is a molded part.

* * * * *

UNITED STATES PATENT AND TRADEMARK OFFICE
CERTIFICATE OF CORRECTION

PATENT NO. : 7,582,264 B2  
APPLICATION NO. : 10/589307  
DATED : September 1, 2009  
INVENTOR(S) : Johan-Valentin Kahl et al.

Page 1 of 1

It is certified that error appears in the above-identified patent and that said Letters Patent is hereby corrected as shown below:

Title Page, Item (75) Inventors: should read

-- (75) Inventors: Kahl; Johan-Valentin (Munich, DE), Zantl; Roman (Baldham, DE), Frank; Michael (Neuss, DE), Trebbe; Uwe (Düsseldorf, DE), Siepmann; Friedhelm (Essen, DE), Thünchen; Andreas (Wuppertal, DE), Stumpe; Stefan (Düsseldorf, DE) --

Signed and Sealed this
Sixteenth Day of August, 2011

David J. Kappos
*Director of the United States Patent and Trademark Office*